United States Patent
Kramer et al.

(10) Patent No.: US 10,872,699 B2
(45) Date of Patent: Dec. 22, 2020

(54) CASE-BASED REASONING IN THE CLOUD USING DEEP LEARNING

(71) Applicants: Martin Kramer, Erlangen (DE); Olivier Pauly, Munich (DE)

(72) Inventors: Martin Kramer, Erlangen (DE); Olivier Pauly, Munich (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 853 days.

(21) Appl. No.: 15/469,310

(22) Filed: Mar. 24, 2017

(65) Prior Publication Data
US 2017/0293736 A1    Oct. 12, 2017

Related U.S. Application Data

(60) Provisional application No. 62/313,433, filed on Mar. 25, 2016.

(51) Int. Cl.
*G16H 50/70* (2018.01)
*G16H 50/20* (2018.01)
(Continued)

(52) U.S. Cl.
CPC .............. *G16H 50/70* (2018.01); *G06F 19/00* (2013.01); *G06F 19/32* (2013.01); *G06N 3/082* (2013.01);
(Continued)

(58) Field of Classification Search
CPC ........ G06N 3/082; G06N 3/084; G06N 20/00; G06N 3/0454; G06N 99/005; G06F 19/00;
(Continued)

(56) References Cited

U.S. PATENT DOCUMENTS 8,644,622 B2    2/2014  Perronnin et al.
9,218,366 B1*  12/2015  Li ..................... G06F 16/5838
(Continued)

FOREIGN PATENT DOCUMENTS

DE    102014207091 A1   10/2015
DE    102014226824 A1    6/2016
WO    WO2012063166 A1    5/2012

OTHER PUBLICATIONS

Liu et al., "Multimodal Neuroimaging Feature Learning for Multiclass Diagnosis of Alzheimer's Disease", Apr. 2015, IEEE Transactions on Biomedical Engineering, vol. 62, No. 4, pp. 1132-1140 (Year: 2015).*
(Continued)

*Primary Examiner* — Robert A Cassity
*Assistant Examiner* — Brent Johnston Hoover
(74) *Attorney, Agent, or Firm* — Lempia Summerfield Katz LLC

(57) ABSTRACT

In order to compare high-dimensional, multi-modal data for a patient to data for other patients, deep learning is used to encode original, multi-modal data for a patient into a compact signature. The compact signature is compared to predetermined compact signatures generated for other patients, and similar predetermined compact signatures are identified based on the comparison. A clinical outcome may be predicted based on the similar predetermined compact signatures that are identified.

15 Claims, 6 Drawing Sheets

(51) Int. Cl.
- G16H 10/60 (2018.01)
- G06N 20/00 (2019.01)
- G06F 19/00 (2018.01)
- G06N 3/08 (2006.01)

(52) U.S. Cl.
CPC ............. *G06N 3/084* (2013.01); *G06N 20/00* (2019.01); *G16H 10/60* (2018.01); *G16H 50/20* (2018.01)

(58) Field of Classification Search
CPC ..... G06F 19/32; G06F 19/3443; G16H 10/60; G16H 50/20; G16H 50/70
See application file for complete search history.

(56) References Cited

U.S. PATENT DOCUMENTS

| | | | |
|---|---|---|---|
| 2011/0026831 A1* | 2/2011 | Perronnin | G06K 9/6277 382/197 |
| 2012/0066000 A1* | 3/2012 | Opfer | G06F 19/325 705/3 |
| 2017/0220854 A1* | 8/2017 | Yang | G06K 9/6288 |

OTHER PUBLICATIONS

European Search Report for European Application No. 17162746.6-1952, dated Jul. 26, 2017.
Hinton, Geoffrey E., and Ruslan R. Salakhutdinov. "Reducing the dimensionality of data with neural networks," Science 313.5786 (2006): 504-507.
Silipo, Rosaria et al., "Seven Techniques for Dimensionality Reduction," available at https://www-cdn.knime.com/sites/default/files/inline-images/knime_seventechniquesdatadimreduction.pdf, pp. 1-21, 2014.
Bar-Hillel Aharon et al., "Learning a Mahalanobis Metric from Equivalence Constraints", Journal of Machine Learning Research, 6 (6), pp. 937-965; 2005.
Clinchant S. et al., "Semantic Combination of Textual and Visual Information in Multimedia Retrieval", Int. Conf. on Multimedia Retrieval; 2011.
Hastie Trevor et al., "Discriminant adaptive nearest neighbor classification", IEEE Transactions on Pattern Analysis and Machine Intelligence, 18(6), pp. 607-616; 1996.
Hertz Homer et al., "Boosting Margin Based Distance Functions for Clustering", International Conference on Machine Learning; 2004.
Hinton G. et al., "Discovering binary codes for documents by learning deep generative models", Topics in Cognitive Science, pp. 1-18; 2010.
Tsymbal, Alexey et al.: "Learning Discriminative Distance Functions for Case Retrieval and Decision Support"; Transactions on Case-Based Reasoning, vol. 3, No. 1, pp. 1-16. ISBN: 978-3-94-050117-2; XP055090974; 2010.
Weinberger Kilian et al., "Distance Metric Learning for Large Margin Nearest Neighbor Classification", Int. Conf. on Neural Information Processing Systems; 2005.
Weinberger Kilian et al., "Distance metric learning for large margin nearest neighbor classification", The Journal of Machine Learning Research, 10, pp. 207-244; 2009.
Woznica Adam et al., Learning to Combine Distances for Complex Representations, Int. Conf. on Machine Learning; 2007.

\* cited by examiner

CASE-BASED REASONING IN THE CLOUD USING DEEP LEARNING

This application is the non-provisional patent application of U.S. Application Ser. No. 62/313,433, the entire contents of which are hereby incorporated by reference in their entirety.

BACKGROUND

The volume of data accumulated and/or produced by institutions and individuals, and including valuable information grows exponentially each year. This is true in the domain of healthcare, where by mining large amounts of data, new correlations, factors, biomarkers, or drugs may be discovered to enhance treatments of tomorrow. Access to this data, however, remains difficult due to the amount of the data and the high-dimensional and multi-modal nature of the data.

Data characterizing patients is acquired and/or extracted from multiple sources of different types of information such as, for example, imaging, laboratory test measurements, and clinical and family history. Modeling similarity of cases using such disparate data types is challenging due to, for example, wide differences in data dimensionality, differences in predictive information content in the various sources, and different scales or structures for different data types.

To leverage the large volume of potentially valuable data, similarity search-based information retrieval may be used. Similarity search-based information retrieval, however, suffers from not being scalable to large amounts of data (e.g., an amount of cases within the data and a number of features within a case) and is unable to process multi-modal data. For example, a particular mode of data, such as imaging, may have 300 variables, while another mode of data has two variables. A classical distance measure employed to assess similarity may produce similarity scores that are dominated by the imaging data at the expense of the minority data source with two variables. In an example where the minority data source is the presence or absence of a recent health event, which is strongly predictive of an outcome, the minority data source is not given enough weight when assessing similarity.

SUMMARY

In order to compare high-dimensional, multi-modal data for a patient to data for other patients, deep learning is used to encode original, multi-modal data for a patient into a compact signature. The compact signature is compared to predetermined compact signatures generated for other patients, and similar predetermined compact signatures are identified based on the comparison. A clinical outcome may be predicted based on the similar predetermined compact signatures that are identified.

In a first aspect, a method for presenting data related to a patient is provided. The method includes identifying, by a processor, a plurality of modality-specific datasets. A first modality-specific dataset of the plurality of modality-specific datasets has a first dimensionality, and a second modality-specific dataset of the plurality of modality-specific datasets has a second dimensionality. The first dimensionality is different than the second dimensionality. The processor generates, with a trained encoder, a first data signature for the first modality-specific dataset and a second data signature for the second modality-specific dataset. A dimensionality of the first data signature is less than the first dimensionality, and a dimensionality of the second data signature is less than the second dimensionality. The dimensionality of the first data signature is the same as the dimensionality of the second data signature. The processor generates, with the trained encoder, a joint signature based on the first data signature and the second data signature as inputs to the trained encoder. The processor transmits the joint data signature to a computing device in communication with and remote from the processor. The processor receives the data related to the patient from the computing device in response to the transmitting of the joint data signature. A representation of the received data related to the patient is displayed.

In a second aspect, a method for identifying first data stored at a first computing device based on second data generated by and received from a second computing device is provided. The first data is related to at least one first patient, and the second data is related to a second patient. The method includes receiving, by a processor of the first computing device, the second data from the second computing device. The second data includes a first data signature. The first data signature is related to the second patient and represents a plurality of modality-specific datasets. The first data signature has a first dimensionality, and a modality-specific dataset of the plurality of modality-specific datasets has a second dimensionality. The first dimensionality is lower than the second dimensionality. The processor compares the first data signature with a plurality of second data signatures stored at the first computing device. The plurality of second data signatures are related to a plurality of first patients, respectively. The plurality of first patients include the at least one first patient. The processor identifies the first data based on the comparison. The first data includes at least one second data signature of the plurality of second data signatures. The processor sends at least a portion of the first data to the second computing device.

In a third aspect, a computing device for presenting data related to a patient is provided. The computing device includes a processor configured to identify a plurality of modality-specific datasets. The plurality of modality-specific datasets is related to the patient. A first modality-specific dataset of the plurality of modality-specific datasets has a first dimensionality, and a second modality-specific dataset of the plurality of modality-specific datasets has a second dimensionality. The first dimensionality is different than the second dimensionality. The processor is further configured to generate, with a trained encoder, a first data signature for the first modality-specific dataset and a second data signature for the second modality-specific dataset. A dimensionality of the first data signature is lower than the first dimensionality, and a dimensionality of the second data signature is lower than the second dimensionality. The dimensionality of the first data signature is the same as the dimensionality of the second data signature. The processor is configured to generate, with the trained encoder, a joint data signature based on the first data signature and the second data signature as inputs to the trained encoder. The processor is further configured to transmit the joint data signature to another computing device. The other computing device is in communication with the computing device via a network. The processor is configured to receive the data related to the patient from the other computing device. The data related to the patient is also related to the transmitted joint data signature. The computing device also includes a display in communication with the processor. The processor is configured to display a representation of the received data.

In a fourth aspect, a computing device for identifying data related to a first patient is provided. The computing device includes a memory configured to store a plurality of first data signatures. Each first data signature of the plurality of first data signatures is related to a respective second patient. The computing device further includes a processor in communication with the memory. The processor is configured to receive a second data signature from another computing device. The second data signature is related to the first patient. The other computing device is in communication with the computing device via a network. The second data signature represents a plurality of modality-specific datasets. The second data signature has a first dimensionality, and a modality-specific dataset of the plurality of modality-specific datasets has a second dimensionality. The first dimensionality is lower than the second dimensionality. The processor is further configured to compare the second data signature with the plurality of first data signatures stored at the memory. The processor is configured to identify the data related to the first patient from the plurality of first data signatures based on the comparison. The data related to the first patient includes at least one first data signature of the plurality of first data signatures. The processor is further configured to send at least a portion of the data related to the first patient to the other computing device.

DETAILED DESCRIPTION OF THE DRAWINGS

The present embodiments provide a case-based reasoning approach to identifying data related to a patient that leverages high-dimensional multi-modal data and processes large amounts of data. To address the challenge of complex multimodal data sources, with varying scale and distribution, an approach based on deep learning is provided. The approach may be a form of non-linear dimensionality reduction.

Original multi-modal patient data describing the patient is encoded into a compact signature that has better properties in terms of scale, distribution, and sparseness compared to the original data. The properties of the compact signature better allow for analysis using, for example, similarity searching compared to the original data.

The compact signature is defined as an activation pattern of neurons of a last hidden layer of a neural network and may be compared using similarity measures such as Hamming distance. Once input into a similarity search engine used with, for example, a K-nearest neighbor (KNN) classification method, the compact nature of the compact signature improves speed and accuracy in retrieval of similar data compared to use of the original data.

The case-based reasoning approach to identifying data of the present embodiments may be used to predict, for example, a clinical outcome. As an example, the case-based reasoning approach may be used to identify a risk for a new patient to develop cardiovascular disease within the next five years based on similar cases (e.g., patients) where information is available.

Implemented as a web service in the cloud and connected to a distributed file system, similar data may be retrieved efficiently by distributing a similarity computation using map-reduced strategy.

Figure 1:
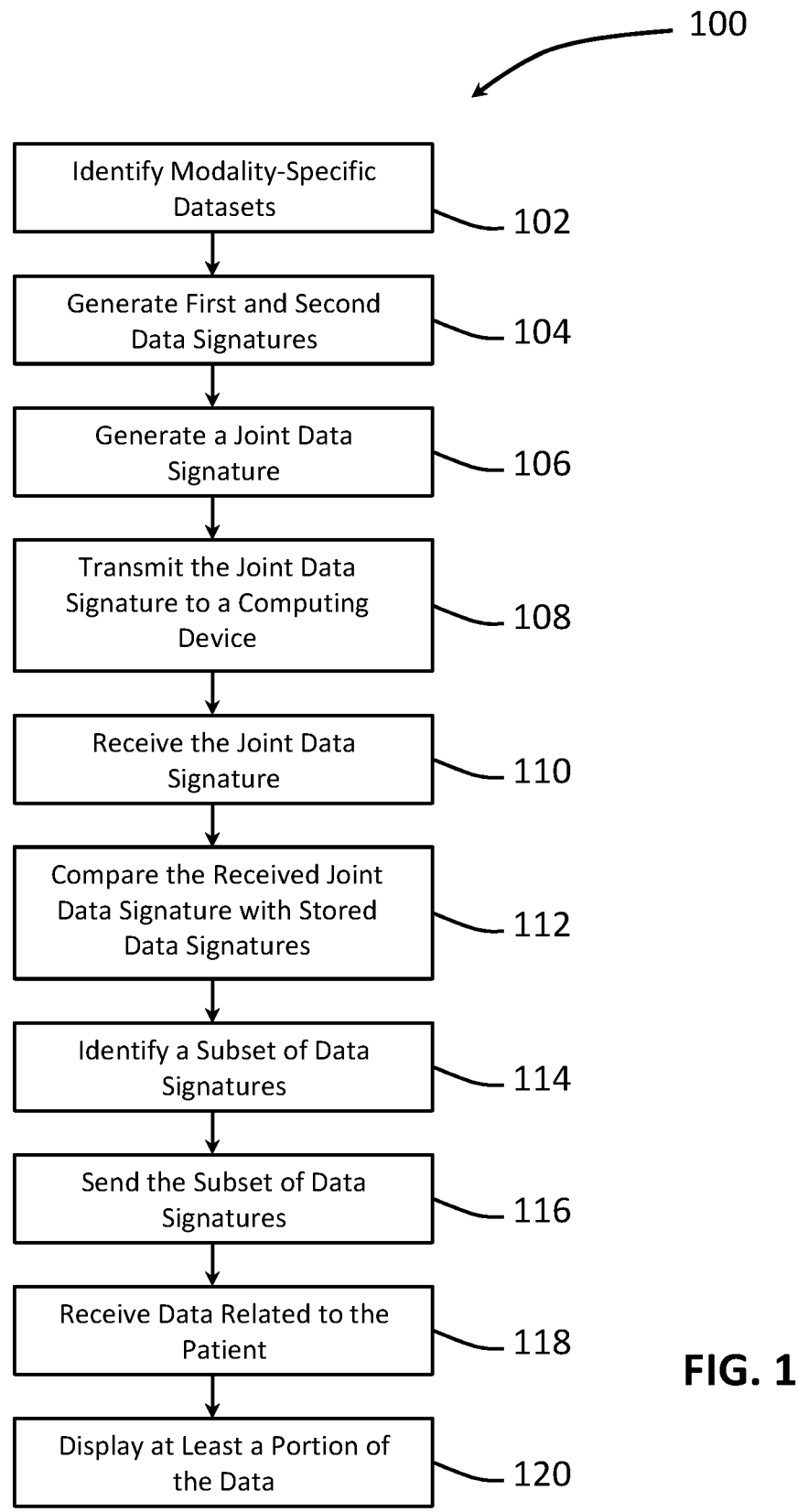
FIG. 1 shows a flowchart of one embodiment of a method for presenting data related to a patient.

FIG. 1 shows a flowchart of one embodiment of a method 100 for presenting data related to a patient. The method 100 may be performed using a system shown in FIG. 6 or another system. The method 100 is implemented in the order shown, but other orders may be used. Additional, different, or fewer acts may be provided. Similar methods may be used for presenting data related to a patient.

In act 102, a first processor (e.g., of a client device) identifies a plurality of modality-specific datasets (e.g., raw data). The plurality of modality-specific datasets may be received from a user via one or more input devices (e.g., a mouse and a keyboard) of the client device, received and/or extracted from a medical device (e.g., a medical imaging device such as a CT device or an MRI device) and/or identified in a memory of the client device or another computing device.

The plurality of modality-specific datasets may be related to a patient. For example, the plurality of modality-specific datasets include datasets representing genetic information, clinical information, parameters from image data, lab results, blood test results, other data, or any combination thereof related to the patient.

At least some modality-specific datasets of the plurality of modality-specific datasets may have different dimensionalities. The dimensionality of a dataset may be defined by a number of parameters of raw data within the dataset (e.g., neural network input parameters). For example, a first modality-specific dataset of the plurality of modality-specific datasets has a first dimensionality, and a second modality-specific dataset of the plurality of modality-specific datasets has a second dimensionality that is different than the first dimensionality. In one example, the first modality-specific dataset represents three parameters, and the second modality-specific dataset represents seven parameters. As examples, higher dimensionality datasets may represent imaging data, while lower dimensionality datasets may represent the presence or absence of a recent health event.

Within the prior art (e.g., a classical distance measure), modeling similarity of cases using such disparate data types is challenging due to wide differences in data dimensionality, differences in predictive information content in the various data sources, and different scales of structure for different data types. Although classical distance measures may be employed to assess similarity of cases based on such disparate data types, results of such an analysis may be treated with caution. For example, if a particular mode of data (e.g., imaging data) yields 300 variables, whereas another mode of data yields only two variables (e.g., a minority data source), a classical distance measure may yield similarity scores that are dominated by the imaging data at the expense of the minority data source. This may be inappropriate if the minority data source is strongly predictive of an outcome (e.g., the presence or absence of a recent health event).

In one or more of the present embodiments, to address the challenge of modeling similarity of cases using disparate data types, a data-driven approach is used. For example, a multimodal, low-dimensional representation is learned from the plurality of modality-specific datasets.

In act 104, the first processor generates, with a trained encoder, a first data signature for the first modality-specific dataset and a second data signature for the second modality-specific dataset. The first data signature and the second data signature have dimensionalities, respectively, that are equal to each other and are lower than both the first dimensionality and the second dimensionality.

Figure 2:
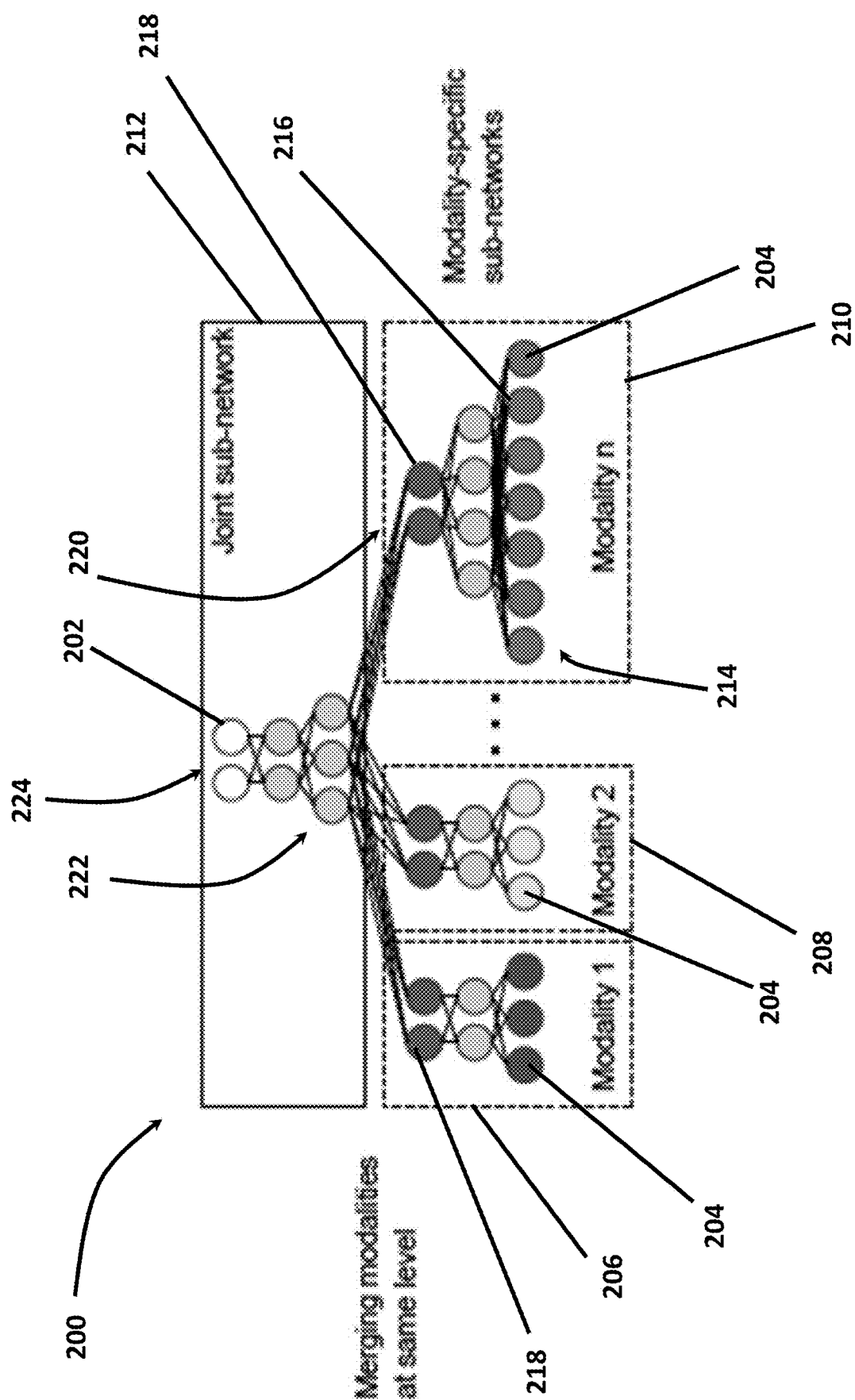
FIG. 2 shows an example of a trained encoder used to generate a joint data signature for multi-modal input data.

FIG. 2 shows an example of a trained encoder 200 used to generate a joint data signature 202 for multi-modal input data 204. The trained encoder 200 (e.g., a multi-modal deep encoder) is a deep neural network including a plurality of modality-specific sub-networks (e.g., 206, 208, and 210) and a joint sub-network 212. The example of FIG. 2 shows three modality-specific sub-networks 206, 208, 210. In other embodiments, more, fewer, and/or different modality-specific sub-networks may be included in the trained encoder 200. Each modality-specific sub-network of the plurality of modality-specific sub-networks 206, 208, and 210 has a respective input layer 214 (e.g., a visible layer). Considering a particular modality, an input for a respective visible layer 214 is raw data. Accordingly, a number of input neurons 216 within the respective visible layer 214 corresponds to the dimensionality of the raw data in the particular modality. The visible layers 214 of the plurality of modality-specific sub-networks 206, 208, and 210, respectively, may thus have different numbers of input neurons 216.

To provide that different modalities have a same influence on a final signature, a same number of output neurons 218 is included within a respective output layer 220 (e.g., a hidden layer) of each modality-specific sub-network of the plurality of modality-specific sub-networks 206, 208, and 210. This results in modality-specific manifolds having a same dimensionality. The hidden layers 220 represent data signatures for the plurality of modality-specific sub-networks 206, 208, and 210, respectively. The first processor, for example, runs the plurality of modality-specific sub-networks 206, 208, and 210 with the raw data input at the input neurons 216 and generates the data signatures 220 for the plurality of modality-specific sub-networks 206, 208, and 210, respectively.

In act 106, the first processor generates, with the trained encoder, a joint data signature based on the first data signature and the second data signature as inputs to the trained encoder. As shown in the example of FIG. 2, the data signatures 220 for the plurality of modality-specific sub-networks 206, 208, and 210, respectively, act as inputs to the joint sub-network 212. In other words, the outputs of the plurality of modality-specific sub-networks 206, 208, and 210 act as inputs to the joint sub-network 212.

Through different hidden layers 222, the joint sub-network 212 merges and further reduces dimensionality. A top layer 224 (e.g., neural activity patterns) of the joint sub-network 212 may be used as the joint data signature 202 that represents the multi-modal input data 204. In the example shown in FIG. 2, all modalities (e.g., the plurality of modality-specific sub-networks 206, 208, and 210) connect together within the joint sub-network 212 at a same level. In other embodiments, however, at least one modality-specific sub-network of the plurality of modality-specific sub-networks 206, 208, and 210 is connected to the joint sub-network 212 at a different level than the other modality-specific sub-networks of the plurality of modality-specific sub-networks 206, 208, and 210.

Figure 3:
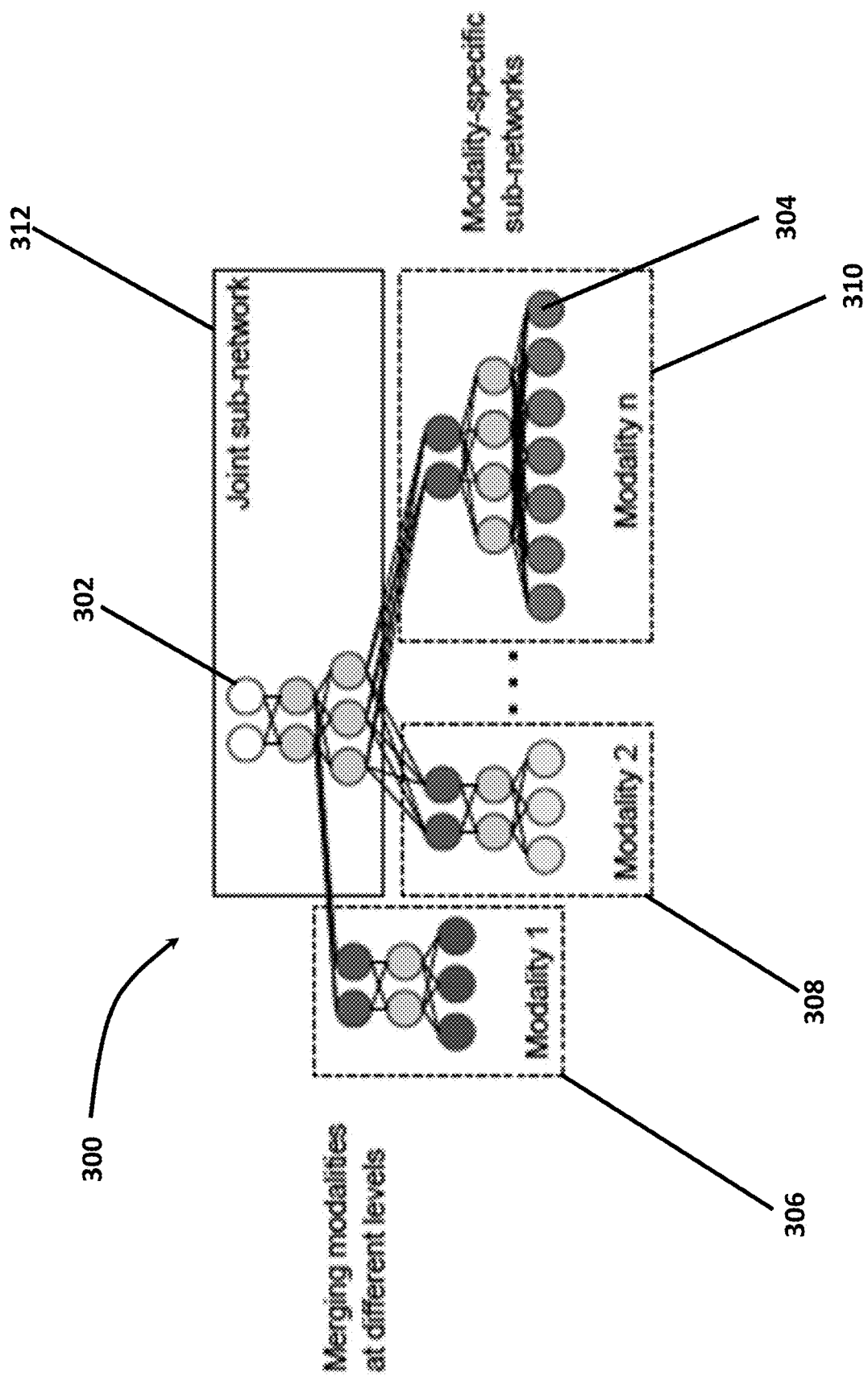
FIG. 3 shows another example of the trained encoder used to generate a joint data signature for multi-modal input data.

FIG. 3 shows another example of a trained encoder 300 used to generate a joint data signature 302 for multi-modal input data 304. A modality-specific sub-network 306 of a plurality of modality-specific sub-networks 306, 308, 310 is connected to a joint sub-network 312 at a different level than the other modality-specific sub-networks 308, 310 of the plurality of modality-specific sub-networks 306, 308, 310. In other embodiments, more, fewer, and/or different modality-specific sub-networks may be connected to a joint sub-network at higher, lower, and/or different levels within the joint sub-network.

The higher the level at which a modality-specific sub-network 306, 308, 310 is connected to the joint sub-network 312, for example, the more influence the modality-specific sub-network 306, 308, 310 has on the joint data signature 302. This permits domain-specific prior knowledge with the network architecture (e.g., causal pathways) to be integrated.

The encoder (e.g., the encoder 200 or 300) may be trained in any number of ways. For example, an encoder may be trained in different ways based on whether target values for the neural network are available. In the context of patient data, an example of a target value is a clinical outcome (e.g., the risk for developing a disease in a predetermined amount of time, such as five years). Supervised training of the encoder 200, for example, may be provided when a real world clinical outcome is known for corresponding known raw input data (e.g., for the input neurons 216). During the process of supervised training, the first processor, for example, optimizes all parameters of the deep neural network (e.g., the encoder) such that a difference between an output of the neural network and the target value (e.g., the known clinical outcome) is minimized. While in the case of regression, sum of square differences may be used, in the case of classification, multi-class cross entropy may be used. The parameters of the deep neural network to be optimized include, for example, weights and bias of all neurons of the deep neural network. The parameters of the deep neural network may be optimized using, for example, a backpropagation algorithm.

Figure 4:
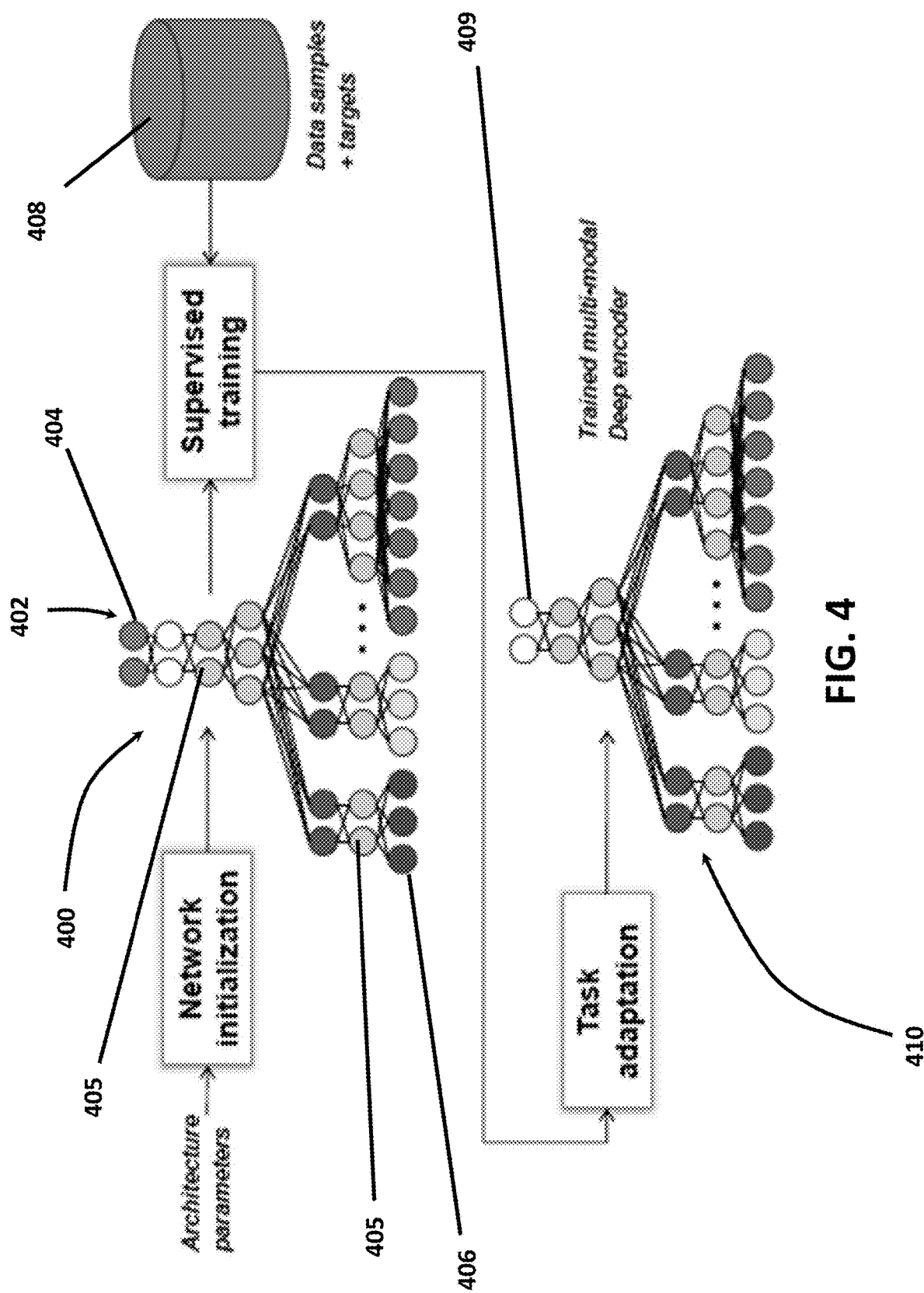
FIG. 4 shows a flowchart of one embodiment for training an encoder.

FIG. 4 shows a flowchart of one embodiment for training an encoder (e.g., a multi-modal neural network). As shown in FIG. 4, the first processor, for example, generates a full multi-modal neural network 400 with one additional layer 402 at the top of the multi-modal neural network 400. The first processor then performs supervised training on the multi-modal neural network 400.

As part of the supervised training, the one additional layer 402 constrains constructions of the multi-modal neural network 400 in that a compact representation 404 (e.g., a joint data signature) of input data 406 input into the multi-modal neural network 400 relates to data included in the additional layer 402 (e.g., related to a clinical outcome). In other words, during training of the encoder 400, optimization of weights associated with neurons of the multi-modal neural network 400 is driven by, for example, the clinical outcome. The input data 406 and the corresponding clinical outcome may be identified within a database 408 (e.g., of the one or more servers within the cloud environment) in communication with, for example, the first processor. For example, the first processor may obtain the input data 406 and the corresponding clinical outcome from the database 408.

In one embodiment, the data included in the additional layer 402 includes a representation of prediction error and a representation of reconstruction error. The weights within the multi-modal neural network are optimized such that the representation of the prediction error and the representation of the reconstruction error are minimized. The first processor may calculate the reconstruction error by using a decoder related to the encoder 400 (e.g., with transposed weights or different weights compared to the encoder 400) to reconstruct inputs, and by comparing the reconstructed inputs with the input data 406 input into the multi-modal neural network 400 as part of the supervised training.

Once the optimization has converged, the first processor, for example, alters (e.g., task adaption) the multi-modal neural network 400, such that the multi-modal neural network 400 outputs a joint data signature 409 as a function of raw input data input to the multi-modal neural network 400. The first processor alters the multi-modal neural network 400 by removing the additional layer 402, and the altered multi-modal neural network 400 is a trained multi-modal deep encoder 410. A remaining top layer of the trained multi-modal deep encoder 410 outputs the joint data signature 409.

Figure 5:
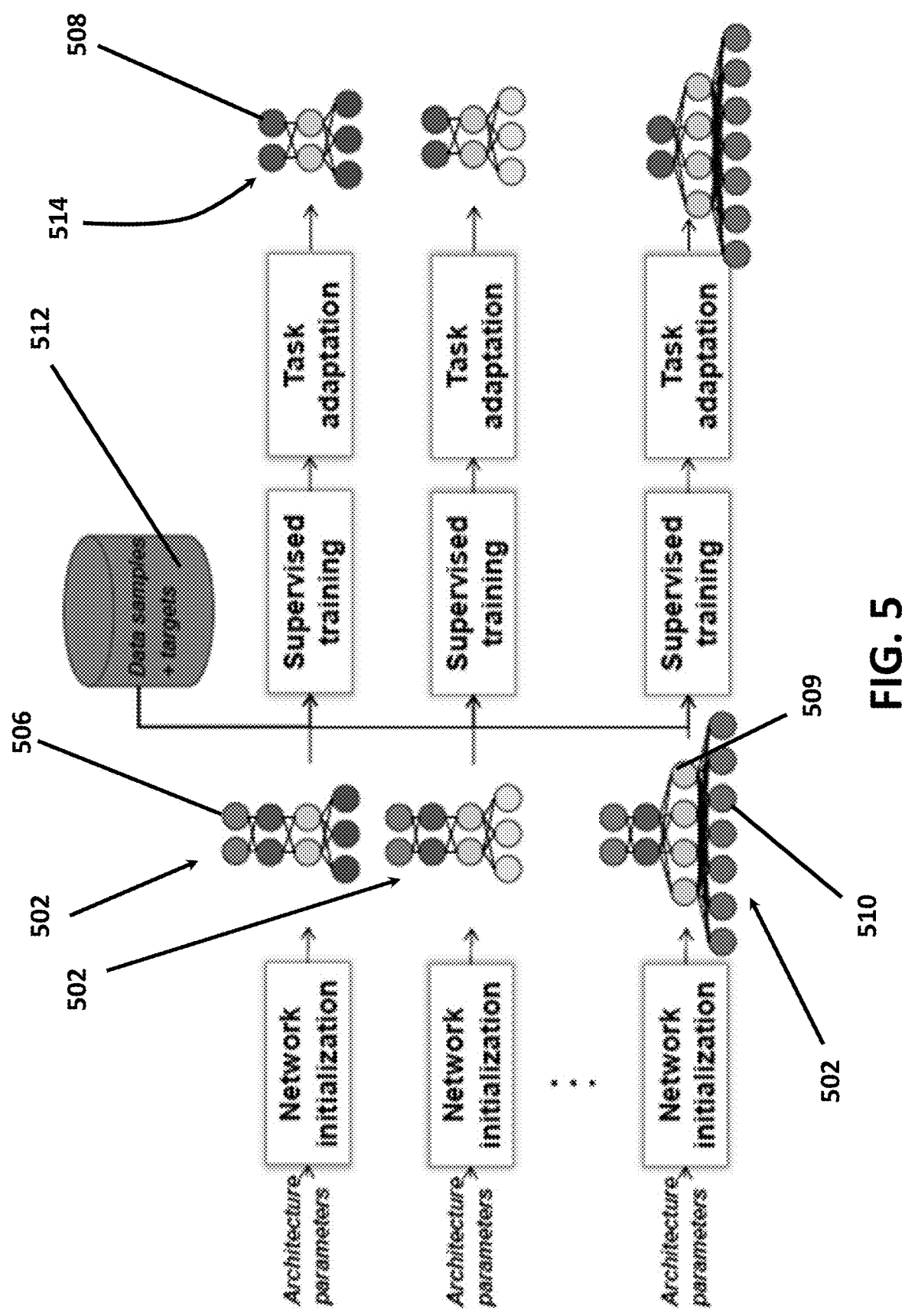
FIG. 5 shows a flowchart of another embodiment for training the encoder.

FIG. 5 shows a flowchart of another embodiment for training an encoder. As shown in FIG. 5, the first processor, for example, generates each modality-specific sub-network of a plurality of modality-specific sub-networks 502 of a full multi-modal neural network. Each modality-specific sub-network 502 is generated with one additional layer 506 at the top of the respective modality-specific sub-network 502. The first processor then performs supervised training for each modality-specific sub-network of the plurality of modality-specific sub-networks 502.

As part of the supervised training, the additional layers 506 constrain constructions of the plurality of modality-specific sub-networks 502, respectively, in that compact representations 508 (e.g., data signatures) of input data 510 input into the plurality of modality-specific sub-networks 502, respectively, relate to data included in the additional layers 506 (e.g., a same clinical outcome for all of the additional layers 506). In other words, during training of the encoder, optimization of weights associated with neurons of the plurality of modality-specific sub-networks 502 is driven by, for example, the clinical outcome. The input data 510 and the corresponding clinical outcome may be identified within a database 512 (e.g., of the one or more servers within the cloud environment) in communication with, for example, the first processor. For example, the first processor may obtain the input data 510 and the corresponding clinical outcome from the database 512.

In one embodiment, the data included in the additional layers 506 includes a representation of prediction error and a representation of reconstruction error. The weights within the plurality of modality-specific sub-networks 502 are optimized such that the representation of the prediction error and the representation of the reconstruction error are minimized. The first processor may calculate the reconstruction error by using a decoder related to the encoder (e.g., with transposed weights or different weights compared to the encoder) to reconstruct inputs, and by comparing the reconstructed inputs with the input data 510 input into the plurality of modality-specific sub-networks 502 as part of the supervised training.

Once the optimizations have converged, the first processor, for example, alters (e.g., task adaption) the plurality of modality-specific sub-networks 502, such that the plurality of modality-specific sub-networks 502 output data signatures as a function of raw input data input to the plurality of modality-specific sub-networks 502. The first processor alters the plurality of modality-specific sub-networks 502 by removing the additional layers 506, and the plurality of altered modality-specific sub-networks 502 are trained modality-specific sub-networks 502. Remaining top layers 514 of the trained modality-specific sub-networks 502 output the data signatures, respectively.

The first processor then generates a full multi-modal neural network (e.g., the encoder) based on the plurality of trained modality-specific sub-networks 502. The first processor generates the full multi-modal neural network with one additional layer at the top of the full multi-modal neural network. The first processor then performs supervised training on the full multi-modal neural network.

In one embodiment, the first processor performs supervised training on the full multi-modal neural network according to the example shown in FIG. 4. The optimized weights of the plurality of modality-specific sub-networks 502 are held constant, and weights of a joint sub-network of the full multi-modal neural network are optimized.

Once the optimization has converged, the first processor alters (e.g., task adaption) the full multi-modal neural network, such that the multi-modal neural network outputs a joint data signature. The first processor alters the full multi-modal neural network by removing the additional layer, and the altered multi-modal neural network is a trained multi-modal deep encoder. A remaining top layer of the trained multi-modal deep encoder outputs the joint data signature.

In one embodiment, when no target values are available (e.g., no clinical outcome corresponding to raw data inputs), a multi-modal neural network may be trained in the same way as an autoencoder is trained. For example, reconstruction of raw input data (e.g., with a decoder) drives optimization. The training may be executed with the example shown in FIG. 4 or the example shown in FIG. 5.

In act 108, the first processor transmits the joint data signature to a computing device in communication with and remote from the processor. For example, the computing device includes one or more servers remote from the processor. The one or more servers may at least partly form a cloud computing environment. The first processor may transmit the joint data signature over a network. The network may, for example, be a wired network or a wireless network.

In act 110, a second processor (e.g., of the one or more servers) receives the joint data signature from the first processor. The computing device (e.g., the cloud computing environment) receives only the joint data signature, or receives the joint data signature and additional data that does not allow the patient to be identified. Accordingly, since the computing device does not have access to the encoder used to generate the joint data signature, and thus the corresponding decoder, the computing device may not back out the raw input data identified at the first processor based on the received joint data signature. This allows raw patient data such as, for example, names and addresses to remain private at the cloud computing side.

In act 112, the second processor compares the received joint data signature with a plurality of data signatures stored in a database of the cloud computing environment. The database may include a distributed file system that stores the plurality of data signatures. The database may, for example, be part of or separate from the one or more servers including the second processor.

The plurality of data signatures correspond to particular patients but do not identify the particular patients. The plurality of data signatures may be stored with or without additional corresponding data. For example, each of the data signatures may be stored with data representing a respective clinical outcome.

The received joint data signature includes two values that represent the patient. Each data signature of the plurality of data signatures stored in the database also includes two values. The received joint data signature and/or each data signature of the plurality of data signatures may include more or fewer values that represent the respective patient.

The second processor compares the received joint data signature with the plurality of data signatures stored in the database by determining a similarity representation between the received joint data signature and each data signature of the plurality of data signatures stored in the database. In one embodiment, the second processor determines the similarity representations using a Hamming distance, an L1 distance, an L2 distance, or another distance for the respective values of the data signatures.

To improve efficiency for similarity computation, a map-reduce strategy may be used. For example, the similarity computation is distributed to a cluster of compute nodes (e.g., of the second processor). Each compute node of the cluster of compute nodes compares the received data signature with a respective portion (e.g., a subset) of data signatures of the plurality of data signatures stored in the database in parallel (e.g., map phase). Once similarity computation is finished by all of the compute nodes, results are gathered and data samples (e.g., corresponding to data signatures stored in the database) are ranked according to similarity to the received data signature (e.g., reduce phase). Only a subset of the data samples are processed and/or sent to the client device.

In act 114, the second processor identifies a subset of data signatures of the plurality of data signatures stored within the database based on the comparison in act 112. In one embodiment, the second processor identifies the subset of data signatures of the plurality of data signatures stored within the database based on a thresholding of the similarity representations determined in act 112. For example, the identified subset of data signatures may correspond to data signatures with determined similarity representations above a predetermined threshold.

In one embodiment, the second processor ranks the subset of data signatures. For example, the second processor may rank the subset of data signatures based on the similarity representations determined in act 114. In other words, a data signature of the subset of data signatures most similar to the received joint data signature is ranked first, and a data signature of the subset of data signatures least similar to the received joint data signature is ranked last. The data signatures of the subset of data signatures may be ordered based on the ranking.

In act 116, the second processor sends the subset of data signatures identified in act 114 and/or a representation of the subset of data signatures identified in act 114 (e.g., data related to the patient) to the client device. The second processor sends the subset of data signatures identified in act 114 and/or a representation of the subset of data signatures identified in act 114 (e.g., a median clinical outcome) to the client device via the network (e.g., wired or wireless). For example, the second processor may send a portion or all data signatures of the subset of data signatures identified in act 114 and/or other data corresponding to the subset of data signatures identified in act 114 to the client device. For example, the second processor may send clinical outcomes corresponding to the subset of data signatures identified in act 114 to the client device.

In one embodiment, the second processor predicts an outcome for the patient based on the subset of data signatures identified in act 114 and sends the predicted outcome to the client device. For example, the second processor may perform a weighted average of the clinical outcomes corresponding to the subset of data signatures identified in act 114 to determine the predicted outcome. Additionally or alternatively, the second processor may extract a mode of distribution from the subset of data signatures identified in act 114. The predicted outcome may be determined in other ways. In one embodiment, the predicted outcome represents a likelihood of a health related event happening within a predetermined amount of time. For example, the predicted outcome may be a percent chance the patient will live a predetermined amount of time (e.g., five years).

In one embodiment, the second processor generates a histogram based on the clinical outcomes corresponding to the subset of data signatures identified in act 114. For example, the second processor may group the clinical outcomes into different intervals of values. In other words, the histogram is computed for the clinical outcomes over a set of retrieved patients (e.g., at least two patients). The generated histogram may represent the predicted outcome. In one embodiment, the second processor sends the generated histogram to the client device instead of or in addition to the subset of data signatures identified in act 114.

In act 118, the client device (e.g., including the first processor) receives the data related to the patient. The first processor receives the data related to the patient from, for example, the second processor. The data related to the patient may include, as discussed above, the subset of data signatures, the corresponding clinical outcomes, the generated histogram, another representation of the subset of data signatures, or any combination thereof. In one embodiment, the second processor does not generate the histogram. Instead, the first processor generates the histogram or the other representation of the subset of data signatures based on the received data related to the patient (e.g., the received clinical outcomes).

In act 120, a display in communication with the first processor (e.g., a display of the client device) displays at least a portion of the data related to the patient. For example, the display presents the generated histogram or another representation of the received data related to the patient. For example, the display displays a representation of the predicted outcome determined by the second processor. In one embodiment, the display presents a life expectancy within a GUI on the display (e.g., similar data signatures predict the patient will live 3.6 years). The display may display other data related to the patient.

In one embodiment, the first processor or the second processor generates additional data, and the client device displays the additional data. The additional data may include a similarity matrix that shows similarities between a query case (e.g., corresponding to the patient) and all retrieved cases (e.g., corresponding to the subset of data signatures). The similarity matrix may be a heat map where high similarities are shown, for example, in colors towards yellow, and low similarities are shown, for example, in colors towards red. The additional data may also include a patient graph with each patient being a colored node. Links are shown as edges between the nodes. Edges or links between cases are defined with similarities. A threshold may be used by the user via the GUI to impact the patient graph (e.g., cuts links if the respective similarity is below a threshold). Within the patient graph, colors correspond to different clusters of nodes.

The range of applications for case-based reasoning solutions in the cloud, as described above with reference to the example of FIG. 1, is very large. For example, within the healthcare domain, the method of FIG. 1, for example, or another method may be used for early diagnosis, screening, decision support, therapy selection, and/or other purposes. When a large database of multi-modal patient data becomes available (e.g., including clinical information, labor test results, and/or imaging data), compact patient signatures may be efficiently learned from the data using the method described with reference to FIG. 1, for example. Attached clinical outcomes (e.g., stored with the compact patient signatures) allow outcome predictions for new incoming patients. Most similar patients may be identified based on the compact patient signatures, and clinical outcomes corresponding to the most similar patients may be aggregated to predict an outcome for a new incoming patient. This permits, for example, a risk for developing a particular disease within a predetermined amount of time to be determined. Additionally or alternatively, this permits, for example, outcomes for different therapies depending on a patient status. Due to the data encoding occurring at the client side (e.g., a hospital), privacy is preserved when a compact data signature generated for the patient at the hospital is sent to the cloud computing environment.

Figure 6:
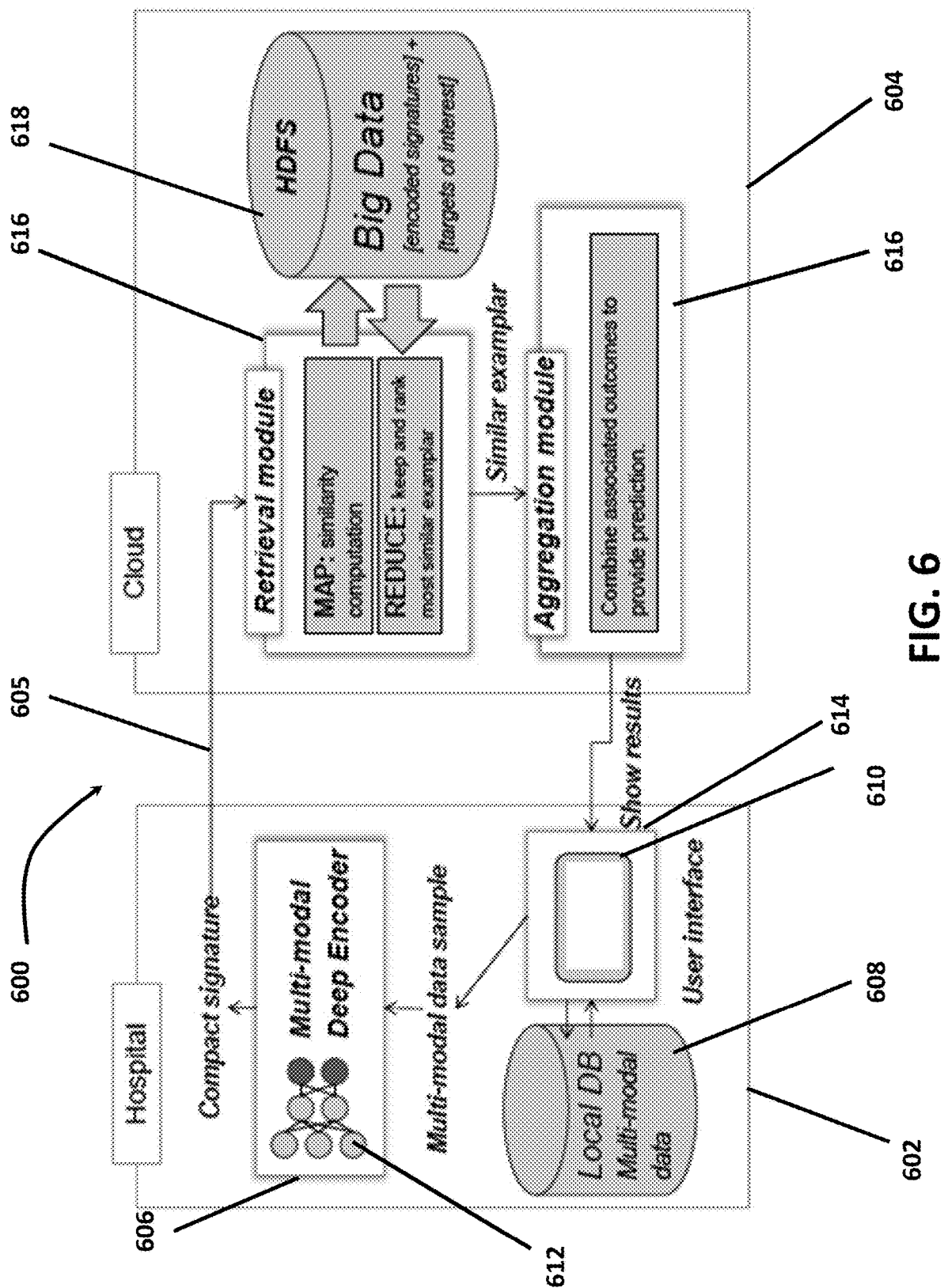
FIG. 6 shows one embodiment of a case-based reasoning system.

FIG. 6 shows one embodiment of a case-based reasoning system 600. The case-based reasoning system 600 or another data system may be used to execute the methods of FIGS. 1, 4, and 5 and/or other methods.

The case-based reasoning system 600 includes a first computing device 602 and a second computing device 604. The second computing device 604 is remote from the first computing device 602, and the first computing device 602 and the second computing device 604 are in communication via a network 605 (e.g., wired or wireless). Data may be sent and received via the network 605 using, for example, HTTPS. As an example, the first computing device 602 is located at a hospital or a doctor's office, and the second computing device 604 is geographically remote from the first computing device 602. The second computing device 604 may form or may be part of a cloud computing environment.

The case-based reasoning system 600 may include more and/or different components. For example, the case-based reasoning system 600 may include a plurality of first computing devices 602 in communication with the second computing device 604 via the network 605 and/or one or more other networks. The plurality of first computing devices 602 may or may not be in communication with each other independent of the second computing device 604.

The first computing device 602 includes a processor 606, a memory 608, and a display 610. The first computing device 602 may include more, fewer, and/or different components. For example, the first computing device 602 may include one or more input devices (not shown) (e.g., a keyboard and a mouse) via which the user may operate the first computing device 602.

The processor 606 is in communication with the memory 608 and the display 610. The processor 606 generates, trains, and runs a multi-modal deep encoder 612. Once the processor 606 generates the multi-modal deep encoder 612, the processor 606 may store the multi-modal deep encoder 612 in the memory 608. The memory 608 may also store any joint data signatures generated by the multi-modal deep encoder 612.

The processor 606 is a general processor, a central processing unit, a control processor, a graphics processor, a digital signal processor, a three-dimensional rendering processor, an image processor, an application-specific integrated circuit, a field-programmable gate array, a digital circuit, an analog circuit, combinations thereof, or other now known or later developed device for image processing. The processor 606 is a single device or multiple devices operating in serial, parallel, or separately. The processor 606 may be a main processor of a computer, such as a laptop or desktop computer, or may be a processor for handling some tasks in a larger system. The processor 606 is configured by instructions, design, hardware, and/or software to perform the acts discussed herein, such as generating the multi-modal deep encoder 612 and/or presenting data related to the patient.

The processor 606 runs the multi-modal deep encoder 612 based on raw patient data (e.g., multi-modal patient data) stored at the memory 608. The memory 608 may receive the multi-modal patient data from various data sources in communication with the first computing device 602. For example, the memory 608 may receive the raw patient data from imaging devices, other memory, and/or other devices.

The memory 608 is a computer readable storage media. The computer readable storage media may include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 608 may be a single device or a combination of devices. The memory 608 may be adjacent to, part of, networked with and/or remote from the processor 606.

Results received from the second computing device 604 via the network 605, for example, may be displayed via a GUI 614 generated by the processor 606 and displayed via the display 610. The GUI 614 may, for example, be a web-based GUI accessible within the hospital intranet. Alternatively or additionally, the processor 606 may generate results based on data received from the second computing device 604 via the network 605, for example, and the display 610 displays the results generated by the processor 606. The display 610 is a monitor, a CRT, an LCD, a plasma screen, a flat panel, a projector or other now known or later developed display device.

The second computing device 604 includes a processor 616 and a memory 618. The second computing device 604 may include more, fewer, and/or different components. For example, the second computing device 604 may include one or more input devices (not shown) (e.g., a keyboard and a mouse) and/or a display (not shown).

The processor 616 is in communication with the memory 618. The processor 616 receives a joint data signature from the first computing device 602 and compares (e.g., similarity computation, map) the received joint data signature with a plurality of predetermined joint data signatures stored at the memory 618. Once a real world clinical outcome occurs for the patient, the received joint data signature may be stored with the corresponding clinical outcome as part of the plurality of predetermined joint data signatures. This is how a database of predetermined joint data signatures is built up.

The processor 616 may also identify a subset of joint data signatures of the plurality of predetermined joint data signatures based on the comparison. For example, the processor 616 may threshold similarity computations for the plurality of predetermined joint data signatures, such that the subset of joint data signatures is formed with cases having a similarity above a threshold. In one embodiment, the processor 616 thresholds the similarity computations by keeping a predetermined number of cases (e.g., the top twenty most similar cases). The user may set the predetermined number of cases via, for example, the GUI 614. Cases corresponding to the subset of joint data signatures may be ranked based on similarity.

The processor 616 may aggregate data (e.g., aggregation module) corresponding to the subset of joint data signatures. For example, a respective clinical outcome may be associated and stored with each joint data signatures of the subset. The processor 616 may process (e.g., combine) data (e.g., the clinical outcomes) associated with the subset of joint data signatures. For example, the processor 616 may generate a histogram based on the clinical outcomes, and transfer the histogram to the first computing device 602 via the network 605 for display.

The processor 616 is a general processor, a central processing unit, a control processor, a graphics processor, a digital signal processor, a three-dimensional rendering processor, an image processor, an application-specific integrated circuit, a field-programmable gate array, a digital circuit, an analog circuit, combinations thereof, or other now known or later developed device for image processing. The processor 616 is a single device or multiple devices operating in serial, parallel, or separately. The processor 616 may be a main processor of a computer, such as one or more servers or desktop computers, or may be a processor for handling some tasks in a larger system. The processor 616 is configured by instructions, design, hardware, and/or software to perform the acts discussed herein, such as comparing data signatures, determining similarities between the data signatures, and/or combining outcomes to provide a prediction.

The plurality of predetermined joint data signatures are stored at the memory 618. The memory 618 may receive the plurality of predetermined joint data signatures all at once, or the memory 618 may receive individual predetermined joint data signatures one at a time from different client devices in communication with the second computing device 604 as real world clinical outcomes are identified for particular patients for which raw input data is known.

The memory 618 is a computer readable storage media. The computer readable storage media may include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 618 may be a single device or a combination of devices. The memory 618 may be adjacent to, part of, networked with and/or remote from the processor 616.

The memory 618 may include a database. For example, the memory 618 may include a distributed file system (e.g., a Java-based file system) that stores a large volume of predetermined joint data signatures with corresponding data (e.g., corresponding clinical outcomes).

While the present claim scope has been described with reference to specific examples, which are intended to be illustrative only and not to be limiting of the claim scope, it will be apparent to those of ordinary skill in the art that changes, additions and/or deletions may be made to the disclosed embodiments without departing from the spirit and scope of the claims.

The foregoing description is given for clearness of understanding only, and no unnecessary limitations should be understood therefrom, as modifications within the scope of the claims may be apparent to those having ordinary skill in the art.

In a first embodiment, a method for presenting data related to a patient is provided. The method includes identifying, by a processor, a plurality of modality-specific datasets. A first modality-specific dataset of the plurality of modality-specific datasets has a first dimensionality, and a second modality-specific dataset of the plurality of modality-specific datasets has a second dimensionality. The first dimensionality is different than the second dimensionality. The processor generates, with a trained encoder, a first data signature for the first modality-specific dataset and a second data signature for the second modality-specific dataset. A dimensionality of the first data signature is less than the first dimensionality, and a dimensionality of the data signature is less than the second dimensionality. The dimensionality of the first data signature is the same as the dimensionality of the second data signature. The processor generates, with the trained encoder, a joint data signature based on the first data signature and the second data signature as inputs to the trained encoder. The processor transmits the joint data signature to a computing device in communication with and remote from the processor. The processor receives the data related to the patient from the computing device in response to the transmitting of the joint data signature. The method includes displaying a representation of the received data related to the patient.

In a second embodiment, with reference to the first embodiment, the plurality of modality-specific datasets include genetic information, clinical information, parameters from image data, lab results, blood test results, or any combination thereof.

In a third embodiment, with reference to the first embodiment, the method further includes training, by the processor, the encoder. The encoder is a neural network. Training the encoder includes identifying, by the processor, input data and a target value associated with the input data, and optimizing, by the processor, the neural network based on the identified input data and target value.

In a fourth embodiment, with reference to the third embodiment, the target value is a predetermined clinical outcome associated with the input data.

In a fifth embodiment, with reference to the third embodiment, the neural network includes modality-specific sub-networks and a joint sub-network. Outputs of the modality-specific sub-networks are inputs to the joint sub-network.

In a sixth embodiment, with reference to the fifth embodiment, optimizing the neural network includes optimizing weights for each neuron of the neural network, such that a difference between an output of the entire neural network, including the modality-specific sub-networks and the joint sub-network, and the identified target value is minimized.

In a seventh embodiment, with reference to the fifth embodiment, optimizing the neural network includes optimizing, for each of the modality-specific sub-networks, weights for each neuron of the respective modality-specific sub-network, such that a difference between an output of the respective modality-specific sub-network and the identified target value is minimized.

In an eighth embodiment, with reference to the seventh embodiment, optimizing the neural network includes optimizing weights for each neuron of the joint sub-network after the weights for the neurons of the modality-specific sub-networks are optimized, such that a difference between an output of the entire neural network, including the modality-specific sub-networks and the joint sub-network, and the identified target value is minimized.

In a ninth embodiment, with reference to the fifth embodiment, at least one of the modality-specific sub-networks connects with the other modality-specific sub-networks at a different level within the joint sub-network.

In a tenth embodiment, a method for identifying first data stored at a first computing device based on second data generated by and received from a second computing device is provided. The first data is related to a plurality of first patients, and the second data is related to a second patient. The method includes receiving, by a processor of the first computing device, the second data from the second computing device. The second data includes a first data signature. The first data signature is related to the second patient and represents a plurality of modality-specific datasets. The first data signature has a first dimensionality, and a modality-specific dataset of the plurality of modality-specific datasets has a second dimensionality. The first dimensionality is lower than the second dimensionality. The processor compares the first data signature with a plurality of second data signatures stored at the first computing device. The plurality of second data signatures are related to the plurality of first patients, respectively. The processor identifies the first data based on the comparison. The first data includes at least one second data signature of the plurality of second data signatures. The at least one second data signature corresponds to at least one first patient of the plurality of first patients, respectively. The processor sends at least a portion of the first data to the second computing device.

In an eleventh embodiment, with reference to the tenth embodiment, the first data signature includes two values representing the first patient. Each second data signature of the plurality of second data signatures includes two values representing a second patient of the plurality of second patients, respectively. Comparing the first data signature with the plurality of second data signatures includes determining a similarity representation between the first data signature and each second data signature of the plurality of second data signatures.

In a twelfth embodiment, with reference to the eleventh embodiment, determining the similarity representations includes determining a similarity representation between the first data signature and each second data signature of the plurality of second data signatures, respectively, using a Hamming distance, an L1 distance, or an L2 distance In a thirteenth embodiment, with reference to the eleventh embodiment, identifying the first data includes identifying the at least one second data signature based on a thresholding of the determined similarity representations.

In a fourteenth embodiment, with reference to the thirteenth embodiment, the method further includes ranking, by the processor, each second data signature of the at least one second data signature based on the determined similarity representations.

In a fifteenth embodiment, with reference to the thirteenth embodiment, the identified first data includes a clinical outcome for each first patient of the at least one first patient. The method further includes predicting, by the processor, an outcome for the second patient based on the clinical outcomes for the at least one first patient, respectively.

In a sixteenth embodiment, with reference to the fifteenth embodiment, predicting the outcome includes performing, by the processor, weighted averaging of the clinical outcomes for the at least one first patient.

In a seventeenth embodiment, with reference to the fifteenth embodiment, the method further includes generating, by the processor, a histogram based on the identified first data. The histogram groups the clinical outcomes for the at least one first patient. The method further includes sending, by the processor, the generated histogram to the second computing device.

In an eighteenth embodiment, a computing device for presenting data related to a patient is provided. The computing device includes a processor configured to identify a plurality of modality-specific datasets. The plurality of modality-specific datasets are related to the patient. A first modality-specific dataset of the plurality of modality-specific datasets has a first dimensionality, and a second modality-specific dataset of the plurality of modality-specific datasets has a second dimensionality. The first dimensionality is different than the second dimensionality. The processor is further configured to generate, with a trained encoder, a first data signature for the first modality-specific dataset and a second data signature for the second modality-specific dataset. A dimensionality of the first data signature is lower than the first dimensionality, and a dimensionality of the second data signature is lower than the second dimensionality. The dimensionality of the first data signature is the same as the dimensionality of the second data signature. The processor is configured to generate, with the trained encoder, a joint data signature based on the first data signature and the second data signature as inputs to the trained encoder, and transmit the joint data signature to another computing device. The other computing device is in communication with the computing device via a network. The processor is further configured to receive the data related to the patient from the other computing device. The data related to the patient is also related to the transmitted joint data signature. The computing device also includes a display in communication with the processor. The display is configured to display a representation of the received data.

In a nineteenth embodiment, with reference to the eighteenth embodiment, the encoder is a neural network. The processor is further configured to identify input data and a target value corresponding to the input data and optimize the neural network based on the identified target value, such that the encoder is trained.

In a twentieth embodiment, a computing device for identifying data related to a first patient is provided. The computing device includes a memory configured to store a plurality of first data signatures. Each first data signature of the plurality of first data signatures is related to a respective second patient. The computing device further includes a processor in communication with the memory. The processor is configured to receive a second data signature from another computing device. The second data signature is related to the first patient. The other computing device is in communication with the computing device via a network. The second data signature represents a plurality of modality-specific datasets. The second data signature has a first dimensionality, and a modality-specific dataset of the plurality of modality-specific datasets has a second dimensionality. The first dimensionality is lower than the second dimensionality. The processor is further configured to compare the second data signature with the plurality of first data signatures stored at the memory, and identify the data related to the first patient from the plurality of first data signatures based on the comparison. The data related to the first patient includes at least one first data signature of the plurality of first data signatures. The processor is configured to send at least a portion of the data related to the first patient to the other computing device.

In connection with any one of the aforementioned embodiments, the computing device for presenting data, the computing device for identifying data, the method for presenting data, or the method for identifying data may alternatively or additionally include any combination of one or more of the previous embodiments.

The foregoing description is given for clearness of understanding only, and no unnecessary limitations should be understood therefrom, as modifications within the scope of the claims may be apparent to those having ordinary skill in the art.

The invention claimed is:

1. A method for presenting data related to a patient, the method comprising:
    identifying, by a processor, a plurality of modality-specific datasets, a first modality-specific dataset of the plurality of modality-specific datasets having a first dimensionality and a second modality-specific dataset of the plurality of modality-specific datasets having a second dimensionality, and the first dimensionality being different than the second dimensionality;
    training, by the processor, an encoder, wherein the encoder is a neural network, wherein the neural network comprises modality-specific sub-networks and a joint sub-network, outputs of the modality-specific sub-networks being inputs to the joint sub-network, wherein at least one of the modality-specific sub-networks connects with the other modality-specific sub-networks at a different level within the joint sub-network, wherein the training results in a trained encoder, and wherein training the encoder comprises:
        identifying, by the processor, input data and a target value associated with the input data; and
        optimizing, by the processor, the neural network based on the identified input data and target value;
    generating, by the processor with the trained encoder, a first data signature for the first modality-specific dataset and a second data signature for the second modality-specific dataset, a dimensionality of the first data signature being less than the first dimensionality and a dimensionality of the second data signature being less than the second dimensionality, the dimensionality of the first data signature being the same as the dimensionality of the second data signature;
    generating, by the processor with the trained encoder, a joint data signature based on the first data signature and the second data signature as inputs to the trained encoder;
    transmitting, by the processor, the joint data signature to a computing device in communication with and remote from the processor;
    receiving, by the processor, the data related to the patient from the computing device in response to the transmitting of the joint data signature; and
    displaying a representation of the received data related to the patient.

2. The method of claim 1, wherein the plurality of modality-specific datasets comprise genetic information, clinical information, parameters from image data, lab results, blood test results, or any combination thereof.

3. The method of claim 1, wherein the target value is a predetermined clinical outcome associated with the input data.

4. The method of claim 1, wherein optimizing the neural network comprises optimizing weights for each neuron of the neural network, such that a difference between an output of the entire neural network, including the modality-specific sub-networks and the joint sub-network, and the identified target value is minimized.

5. The method of claim 1, wherein optimizing the neural network comprises optimizing, for each of the modality-specific sub-networks, weights for each neuron of the respective modality-specific sub-network, such that a difference between an output of the respective modality-specific sub-network and the identified target value is minimized.

6. The method of claim 5, wherein optimizing the neural network comprises optimizing weights for each neuron of the joint sub-network after the weights for the neurons of the modality-specific sub-networks are optimized, such that a difference between an output of the entire neural network, including the modality-specific sub-networks and the joint sub-network, and the identified target value is minimized.

7. A method for identifying first data stored at a first computing device based on second data generated by and received from a second computing device, the first data being related to a plurality of first patients and the second data being related to a second patient, the method comprising:
    receiving, by a processor of the first computing device, the second data from the second computing device, wherein the second data comprises a first data signature, the first data signature being related to the second patient and representing a plurality of modality-specific datasets, wherein the first data signature has a first dimensionality and a modality-specific dataset of the plurality of modality-specific datasets has a second dimensionality, the first dimensionality being lower than the second dimensionality;
    comparing, by the processor, the first data signature with a plurality of second data signatures stored at the first computing device, wherein the plurality of second data signatures is related to the plurality of first patients, respectively, wherein the first data signature includes two values representing the second patient, and wherein each second data signature of the plurality of second data signatures includes two values representing a patient of the plurality of first patients, respectively, and wherein the comparing comprises determining a similarity representation between the first data signature and each second data signature of the plurality of second data signatures;
    identifying, by the processor, the first data based on the comparison, wherein the first data comprises at least one second data signature of the plurality of second data signatures, the at least one second data signature corresponding to the at least one first patient of the plurality of first patients, respectively, and wherein the identifying further comprises identifying the at least one second data signature based on a comparison of the determined similarity representations to a threshold; and
    sending, by the processor, at least a portion of the first data to the second computing device.

8. The method of claim 7, wherein determining the similarity representations comprises determining a similarity representation between the first data signature and each second data signature of the plurality of second data signatures, respectively, using a Hamming distance, an L1 distance, or an L2 distance.

9. The method of claim 7, further comprising ranking, by the processor, each second data signature of the at least one second data signature based on the determined similarity representations.

10. The method of claim 7, wherein the identified first data includes a clinical outcome for each first patient of the at least one first patient, and wherein the method further comprises predicting, by the processor, an outcome for the second patient based on the clinical outcomes for the at least one first patient, respectively.

11. The method of claim 10, wherein predicting the outcome comprises performing, by the processor, weighted averaging of the clinical outcomes for the at least one first patient.

12. The method of claim 10, further comprising:
generating, by the processor, a histogram based on the identified first data, the histogram grouping the clinical outcomes for the at least one first patient; and
sending, by the processor, the generated histogram to the second computing device.

13. A computing device for presenting data related to a patient, the computing device comprising:
a processor configured to:
identify a plurality of modality-specific datasets, the plurality of modality-specific datasets being related to the patient, a first modality-specific dataset of the plurality of modality-specific datasets having a first dimensionality and a second modality-specific dataset of the plurality of modality-specific datasets having a second dimensionality, and the first dimensionality being different than the second dimensionality;
train, by the processor, an encoder, wherein the encoder is a neural network, wherein the neural network comprises modality-specific sub-networks and a joint sub-network, outputs of the modality-specific sub-networks being inputs to the joint sub-network, wherein at least one of the modality-specific sub-networks connects with the other modality-specific sub-networks at a different level within the joint sub-network, wherein the training results in a trained encoder, and wherein training the encoder comprises:
identification, by the processor, of input data and a target value associated with the input data; and
optimization, by the processor, of the neural network based on the identified input data and target value;
generate, with the trained encoder, a first data signature for the first modality-specific dataset and a second data signature for the second modality-specific dataset, a dimensionality of the first data signature being lower than the first dimensionality and a dimensionality of the second data signature being lower than the second dimensionality, the dimensionality of the first data signature being the same as the dimensionality of the second data signature;
generate, with the trained encoder, a joint data signature based on the first data signature and the second data signature as inputs to the trained encoder;
transmit the joint data signature to another computing device, the other computing device being in communication with the computing device via a network; and
receive the data related to the patient from the other computing device, the data related to the patient also being related to the transmitted joint data signature; and
a display in communication with the processor, the display being configured to display a representation of the received data.

14. The computing device of claim 13, wherein the encoder is a neural network, and
wherein the processor is further configured to identify input data and a target value corresponding to the input data and optimize the neural network based on the identified target value, such that the encoder is trained.

15. A computing device for identifying data related to a first patient, the computing device comprising:
a memory configured to store a plurality of first data signatures, each first data signature of the plurality of first data signatures being related to a respective second patient;
a processor in communication with the memory, the processor being configured to:
receive a second data signature from another computing device, the second data signature being related to the first patient, the other computing device being in communication with the computing device via a network, the second data signature representing a plurality of modality-specific datasets, the second data signature having a first dimensionality, and a modality-specific dataset of the plurality of modality-specific datasets having a second dimensionality, the first dimensionality being lower than the second dimensionality, the second data signature including two values representing the first patient, and each first data signature of the plurality of first data signatures including two values representing a patient of the plurality of second patients, respectively;
compare the second data signature with the plurality of first data signatures stored at the memory;
determine a similarity representation between the second data signature and each first data signature of the plurality of first data signatures;
identify the data related to the first patient from the plurality of first data signatures based on the comparison, the data related to the first patient comprising at least one first data signature of the plurality of first data signatures;
identify the at least one first data signature based on a comparison of the determined similarity representations to a threshold; and
send at least a portion of the data related to the first patient to the other computing device.

* * * * *